United States Patent [19]

Abt

[11] Patent Number: 4,797,424

[45] Date of Patent: Jan. 10, 1989

[54] SALINE SOLUTION FOR FROZEN FOAM

[76] Inventor: Nancy G. Abt, 9397 Midnight Pass Rd., #404S, Sarasota, Fla. 34242

[21] Appl. No.: 157,598

[22] Filed: Feb. 19, 1988

[51] Int. Cl.$^4$ .............................................. C08J 9/36
[52] U.S. Cl. ...................................... 521/53; 264/28; 521/55; 521/918; 428/320.2
[58] Field of Search ........................ 521/53, 55, 918; 264/28; 428/320.2

[56] References Cited

U.S. PATENT DOCUMENTS

| | | | |
|---|---|---|---|
| 2,354,744 | 8/1944 | Dreyfus | 264/28 |
| 3,535,143 | 10/1970 | Shkapenko et al. | 521/918 |
| 4,641,655 | 2/1987 | Abt | 128/380 |

Primary Examiner—William J. Van Balen
Attorney, Agent, or Firm—Charles J. Prescott; Raymond H. Quist

[57] ABSTRACT

A frozen open-celled material is prepared by saturating the material with a solution of 30 to 60 grams of salt to one liter of water. Preferably from 40 to 50 grams of salt to one liter of water. The saturated material, preferably open-celled polyurethane foam, is then frozen. Deterioration of the foam which occurs when plain water is used is essentially eliminated.

6 Claims, No Drawings

SALINE SOLUTION FOR FROZEN FOAM

BACKGROUND OF THE INVENTION

1. Field of the Invention

This invention relates generally to a solution for use in preparing frozen foam, and more particularly to a solution which minimizes damage to the foam.

2. Description of Related Art

In my previous U.S. Pat. No. 4,641,655, entitled: "Therapeutic Cooling Wrap", I disclosed a cooling wrap having a pouch for containing a frozen water medium such as ice or open-celled foam saturated with water and frozen. Since that time I have discovered that the foam tends to deteriorate and break apart with repeated cycles of freezing and melting. I have now found that this deterioration can be essentially eliminated or at least greatly minimized by using a salt solution. Moreover, I have found the use of a saline solution of sodium chloride and fresh water within certain ranges to have additional beneficial results.

It is therefore an object of this invention to provide a solution for use in freezing open-celled material.

It is also an object of this invention to provide a frozen foam which takes a longer time to completely melt than frozen foam made with plain water.

It is a further object of this invention to provide a solution for a frozen foam which permits repeated cycles of freezing and thawing while minimizing damage to the foam.

In accordance with these and other objects, which will become apparent hereafter, the instant invention will now be described.

SUMMARY OF THE INVENTION

An open-celled material, such as open-celled polyurethane foam, is saturated with a solution made using 30 to 60 grams of a salt, such as sodium chloride, to 1 liter of water. Preferably using 40 to 50 grams of salt to 1 liter of water. The saturated material is then frozen for later use, such as in a therapeutic cooling wrap. The use of these solutions minimizes deterioration of the foam which occurs when using plain water and also has greater cooling capacity than frozen foam prepared with plain water.

DETAILED DESCRIPTION OF THE INVENTION

Solutions have been prepared of various concentrations of solids and liquids using water as the solvent. These solutions have a lower freezing temperature than plain water. Polyurethane open-celled foam and natural sponge samples were saturated with the solutions and placed in a freezer having a temperature of between $-12$ and $-14$ degrees C. After allowing a sufficient time for freezing, the samples were removed and examined.

Certain solutions were found to be unsatisfactory for various reasons. Solutions made using denatured alcohol as the solute were rejected because of the odor and the toxicity. Some solutions had insufficient solute to cure the problem of damage to the open-celled materials. Some solutions had so much solute that the samples did not freeze completely and had no discernible ice crystals.

Solutions using salt as the solute within the range of 30 to 60 grams of salt (sodium chloride) to 1 liter of water were found to be useful in eliminating or minimizing damage to the open-celled foam. Salt solutions within the range of 40 to 50 grams of salt to 1 liter of water are preferably used because they provide a combination of high cooling capacity with minimum foam deterioration. The high cooling capacity is desirable since it extends the time before the open-celled material must be replaced with new frozen material.

When the frozen open-celled material is used in my patented therapeutic cooling wrap, the melting salt solution is applied to the skin. I believe the presence of the salt solution on the skin has an additional beneficial physiological effect over the use of plain water because I find I fatigue less quickly.

Although the salt solutions eliminate or minimize damage to the natural sponge, this material is not preferred because of the non-uniformity of the cells and the difficulty in shaping it to desired configurations. For the purpose of frozen foam to be used in the cooling wrap I have used open-celled polyurethane foam; however, other synthetic open-celled foam materials may also be useful. I also prefer using a blue foam as it is more closely associated with coolness.

Although the only salt I tested for this purpose was ordinary table salt, it appears other salts would provide at least some of the same benefits. A solution in accordance with the invention may be made by adding one and one half teaspoons of salt to eight ounces of water.

While the instant invention has been described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent methods.

I claim:

1. A method of preparing a frozen open-celled material comprising the steps of:
   combining a salt with fresh water in a ratio of from 30 gms of salt to 1 liter of water, to 60 gms of salt to 1 liter of water to form a solution;
   saturating an open-celled material in said solution; and
   freezing said saturated open-celled material.

2. A method in accordance with claim 1 wherein: said salt is sodium chloride.

3. A method in accordance with claim 1 wherein: said open-celled material is a polyurethane foam.

4. A method in accordance with claim 1 wherein: the ratio is from 40 gms of salt to 1 liter of water, to 50 grams of salt to one liter of water.

5. A method of preparing a frozen open-celled polyurethane foam comprising the steps of:
   preparing a saline solution of from 40 to 50 grams of salt to 1 liter of water;
   saturating the open-celled polyurethane foam with said solution; and
   freezing said saturated foam.

6. A frozen foam comprising:
   an open-cell foam material saturated with a saline solution of from 40 to 50 grams of salt to 1 liter of water and frozen.

* * * * *